(12) United States Patent
George et al.

(10) Patent No.: US 10,194,830 B2
(45) Date of Patent: Feb. 5, 2019

(54) HIGH TEMPORAL RESOLUTION MONITORING OF CONTACT BETWEEN CATHETER TIP AND TARGET TISSUE DURING A REAL-TIME-MRI-GUIDED ABLATION

(71) Applicant: UNIVERSITY OF UTAH RESEARCH FOUNDATION, Salt Lake City, UT (US)

(72) Inventors: Ashvin Kurian George, Urbana, IL (US); Evgueni G. Kholmovski, Salt Lake City, UT (US); Nassir F. Marrouche, Park City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 297 days.

(21) Appl. No.: 14/208,435

(22) Filed: Mar. 13, 2014

(65) Prior Publication Data
US 2014/0275972 A1   Sep. 18, 2014

Related U.S. Application Data

(60) Provisional application No. 61/791,987, filed on Mar. 15, 2013.

(51) Int. Cl.
*A61B 5/06* (2006.01)
*A61B 5/00* (2006.01)
(Continued)

(52) U.S. Cl.
CPC ............. *A61B 5/062* (2013.01); *A61B 5/055* (2013.01); *A61B 5/6852* (2013.01); *A61B 18/1492* (2013.01); *A61B 34/20* (2016.02); *A61B 5/0402* (2013.01); *A61B 2017/00243* (2013.01); *A61B 2018/00357* (2013.01); *A61B 2018/00577* (2013.01); *A61B 2034/2051* (2016.02); *A61B 2090/374* (2016.02)

(58) Field of Classification Search
None
See application file for complete search history.

(56) References Cited

U.S. PATENT DOCUMENTS

2007/0135705 A1* 6/2007 Lorenz ................... A61B 5/055
                                                        600/410
2009/0177111 A1* 7/2009 Miller .................... A61B 5/053
                                                        600/547

OTHER PUBLICATIONS

Moore's law From Wikipedia, the free encyclopedia pub. online on Feb. 27, 2013, URL: https://en.wikipedia.org/w/index.php?title=Moore%27s_law&oldid=540958859.*

(Continued)

*Primary Examiner* — Katherine Fernandez
*Assistant Examiner* — Michael Kellogg
(74) *Attorney, Agent, or Firm* — Michael Best & Friedrich LLP (57) ABSTRACT

A method of monitoring a position of a catheter tip relative to a target tissue. The method includes steps of identifying a wall structure in the target tissue; guiding a catheter towards the wall structure; monitoring a location of the catheter; directing a navigator beam towards the wall structure; aligning the navigator beam with the location of the catheter; monitoring a position of the wall structure using the navigator beam; and determining the position of the wall structure relative to the location of the catheter.

19 Claims, 5 Drawing Sheets

(51) Int. Cl.
*A61B 5/055* (2006.01)
*A61B 18/14* (2006.01)
*A61B 34/20* (2016.01)
A61B 5/0402 (2006.01)
A61B 17/00 (2006.01)
A61B 18/00 (2006.01)
A61B 90/00 (2016.01)

(56) References Cited

OTHER PUBLICATIONS

Coronary MR Angiography: Selection of Acquisition Window of Minimal Cardiac Motion with Electrocardiography-triggered Navigator Cardiac Motion Prescanning—Initial Results by Wang et al. pub. Radiology 2001; 218:580-585.*

Continual NMR Cardiography without Gating: M-Mode MR Imaging by Pearlman et al. pub. Radiology 1990; 175:369-373.*

Real-Time Acquisition, Display, and Interactive Graphic Control of NMR Cardiac Profiles and Images by Hardy et al. pub. MRM 29:667473 (1993).*

Digital Image Processing: PIKS Scientific Inside, Fourth Edition, by William K. Pratt Copyright © 2007 by John Wiley & Sons, Inc. Ch 15 Edge Detection pp. 465-533 ISBN-10: 0471767778; Published Online: Jun. 14, 2006.*

Vergara et al., "Real Time MRI Guided Radiofrequency Atrial Ablation and Visualization of Lesion Formation at 3-Tesla" Heart Rhythm. Feb. 2011; 8(2): 295-303.

Bornert et al., "On spatially selective RF excitation and its analogy with spiral MR image acquisition" Magnetic Resonance Materials in Physics, Biology and Medicine 7 (1998) 166-178.

* cited by examiner

FIG. 7b ed in the atrial wall to isolate the sources/triggers of abnormal electrical activity. The success rate of RF ablation is limited by the poor imaging that is currently clinically available, generally using X-ray projection imaging and intracardiac echo (ICE). X-ray imaging has poor soft-tissue contrast and only provides projection views. Ultrasound/ICE catheter positioning is cumbersome and provides only limited wall visualization. Visualization of the catheter tip visualization over a static atrial shell does not provide real-time relative positioning of the catheter tip and the wall.

Poor imaging guidance results in the inaccurate deposition of RF energy and, consequently, can lead to errors in the intended locations of the scars. This may result in the incomplete electrical isolation of the arrhythmia triggers and, in turn, the recurrence of symptoms.

SUMMARY

Accordingly, disclosed herein is a novel method to monitor the contact made between the catheter tip and the target tissue during real-time-MRI-guided radiofrequency (RF) ablation.

In one embodiment, the invention provides a method of monitoring a position of a catheter tip relative to a target tissue. The method includes steps of identifying a wall structure in the target tissue; guiding a catheter towards the wall structure; monitoring a location of the catheter; directing a navigator beam towards the wall structure; aligning the navigator beam with the location of the catheter; monitoring a position of the wall structure using the navigator beam; and determining the position of the wall structure relative to the location of the catheter.

HIGH TEMPORAL RESOLUTION MONITORING OF CONTACT BETWEEN CATHETER TIP AND TARGET TISSUE DURING A REAL-TIME-MRI-GUIDED ABLATION

CROSS REFERENCE TO RELATED APPLICATIONS

This application claims priority to U.S. Provisional Application No. 61/791,987, filed Mar. 15, 2013, which is incorporated herein by reference in its entirety.

BACKGROUND

The present invention relates to real-time-MRI-guided radiofrequency (RF) cardiac tissue ablation.

Real-time-MRI-guided radiofrequency (RF) cardiac tissue ablation can be used for treatment of conditions such as cardiac arrhythmias including atrial fibrillation (AF). RF ablation is a minimally-invasive catheter-based procedure in which RF energy is used to create lesions in the atrial wall in a prescribed manner to isolate ectopic electrical activity.

During RF ablation procedures, accurate knowledge of contact made between catheter tip and the structure to be treated, for example the left atrial (LA) wall, is crucial for success of creating the lesion, for accurate electrocardiogram measurement, and for ensuring patient safety.

However, the monitoring of tip-tissue contact, which is currently being performed using X-ray or ultrasound technologies, is a known shortcoming of current real-time MRI technology. During RF ablation, commonly used to treat cardiac arrhythmias such as atrial fibrillation, scars are intentionally creat In another embodiment the invention provides a system for monitoring a position of a catheter tip relative to a target tissue. The system includes a magnetic resonance imaging (MRI) system, a catheter including a position tracking system and ablation and electrogram recording electrodes, and a controller in communication with the MRI system and the catheter. The controller is configured to identify a wall structure in the target tissue, monitor a location of the catheter during guidance of the catheter towards the wall structure, direct a navigator beam towards the wall structure, align the navigator beam with the location of the catheter, report a position of the wall structure using the navigator beam, and determine the position of the wall structure relative to the location of the catheter.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

During an RF ablation, commonly used to treat cardiac arrhythmias, a catheter is percutaneously inserted into a vein or artery and maneuvered into a heart chamber under the guidance of real-time magnetic resonance imaging (MRI). Once the catheter is in an appropriate position, and electrode at the end of the catheter is used to ablate cardiac tissue. As discussed above, however, improved techniques are required for monitoring a position of the catheter relative to the intended target of the catheter, which is often the atrial wall.

Disclosed herein are methods and systems for visualizing and monitoring the contact made between the target tissue, for example the wall of a beating heart, and the electrodes at the distal end of the catheter. It is necessary to monitor this tip-tissue contact in order to (a) effectively deliver RF energy by ensuring contact between the heat source and the target, and (b) better evaluate the quality of an ablation from the electrogram. The quality of the ablation is judged by estimating the post-ablation reduction of the signal measured by the electrodes at the catheter tip. However, poor imaging makes it hard to determine if the reason for a reduced signal is a successful ablation or the lack of contact between the catheter tip and the target tissue. Accordingly, disclosed are methods and systems for using a pencil beam navigator, positioned at the catheter tip and perpendicular to the atrial wall, in order to automatically detect wall location at a high resolution. Combining this with real-time catheter tracking permits for real-time monitoring of tip-tissue contact.

The disclosed methods and systems use a navigator beam (such as an MRI pencil-beam navigator, an MRI technique in which a column-shaped volume is excited and a 1D signal is acquired) combined with a real-time-MRI sequence which is capable of tracking the 3D curve of the catheter in real-time. Using this apparatus, the position of the target tissue relative to the catheter tip is determined by automatically positioning the navigator beam so that it is aligned perpendicular to the target tissue (such as the heart wall, the approximate location of which is known from a pre-procedure MRI scan) and concentric with the axis of the catheter tip (the location of which is known from real-time tracking).

The location of the heart wall is determined from the navigator signal by visualization of the raw signal or automatic detection by image processing. In various alternative embodiments, improved monitoring may be obtained by using a 2D echoplanar projection readout of the excited pencil-beam volume instead of the 1D projection proposed above. Improved monitoring may also be obtained by enhancing blood-tissue contrast by modifying the imaging parameters to conform to balanced-steady-state-free-precession.

While the state-of-the-art real-time MRI technology allows for the imaging of an MR slice, whose position can be interactively modified, at a temporal resolution of about 4 frames/second, this is insufficient to monitor tip-tissue contact. The advantages of the disclosed methods and systems include that they (1) achieve a higher temporal resolution, of up to about 50 frames/second, (2) avoid the need for the operator to explicitly reposition the imaging slice, (3) are able to monitor to the local volume around the target rather than merely a thin slice through it, and (4) provide a dedicated visualization of the tip-tissue interface (e.g. through an M-mode-like display).

In various embodiments, the higher temporal resolution achieved using the disclosed methods and systems includes rates of up to about 5 frames/second, up to about 10 frames/second, up to about 20 frames/second, up to about 30 frames/second, or up to about 40 frames/second. The term 'frames' is used broadly to indicate various observation points that provide an indication of a position of a structure such as a heart wall at a particular time period.

The disclosed methods and systems are applicable to various real-time MRI guidance technologies that make use of a catheter. These include a variety of minimally-invasive procedures including ablation procedures for cardiac arrhythmias and the repair of congenital and other mechanical heart defects.

Various embodiments of the methods and systems disclosed herein may be implemented on an MRI system to provide features including real-time sequences, combination with catheter tracking, and automated placement and detection of structures.

Figure 1:
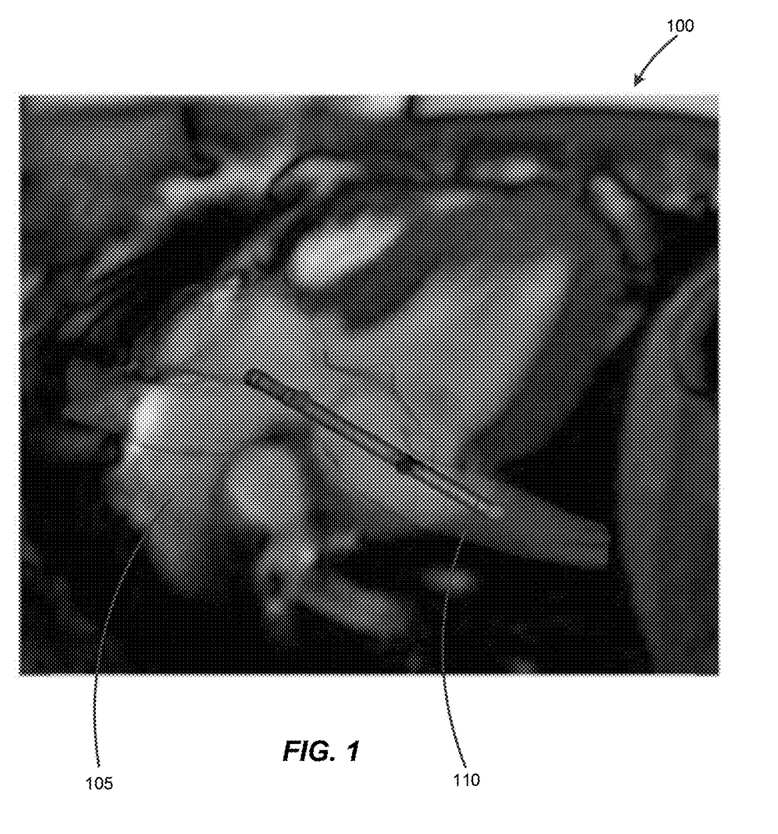
FIG. 1 shows a real-time MRI display with a catheter superimposed on an image of a heart.

Under the current real-time MRI paradigm, as shown in FIG. 1, a single slice 100, whose location and orientation are modified interactively by the operator, is imaged continuously with a spatial resolution of about 2 mm and a frame rate of 3 to 4 frames per second. In addition, a 3D static shell of the atrium 105, extracted from an MR angiography scan acquired at the start of the procedure, and a diagram of the catheter 110, tracked in real-time using four tracking coils located on the catheter shaft, are displayed. The temporal and spatial resolution provided by this display is sufficient while the operator navigates the device towards the target but during the actual ablation of a target it would be beneficial for the operator to be able to switch to an imaging mode in which visualization is provided solely by a static shell 105, the diagram of the moving catheter 110, and the real-time pencil beam navigator display.

Figure 2:
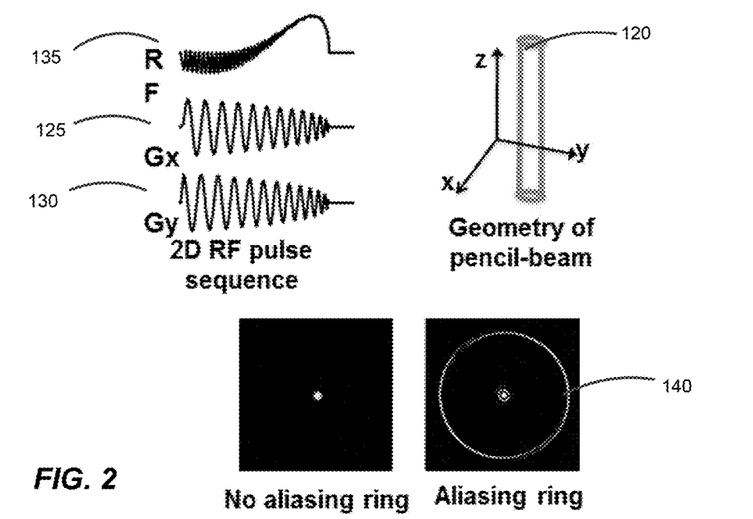
FIG. 2 shows a diagram of how an MRI pencil beam navigator is formed.

FIG. 2 provides a diagram showing how an MRI pencil beam navigator 120 is formed. A spiral gradient (pulse sequence indicated by 'Gx', 'Gy') 125, 130 is played concurrently with a shaped RF pulse ('RF')135, as shown in the top left of FIG. 2, to produce a circular excitation profile, followed by a readout and a spoiler gradient. This produces a narrow 'pencil' beam 120 as shown in the top right of FIG. 2.

In one embodiment, the pencil-beam navigator 120 is implemented using a 2D RF excitation, in which a spiral gradient 125, 130 is played concurrently with an RF pulse 135.

The gradient 125,130 determines the k-space traversal of the beam 120 and the RF amplitude determines the shape of the excitation region. Factors that should be taken into consideration when adjusting the parameters include the fact that the pulse length is limited by T2-relaxation effects and that there is a tradeoff between the sharpness of the profile vs. producing an alias ring artifact 140 (bottom of FIG. 2). In general the diameter of the pencil beam 120 according to embodiments of the invention is in the range of 2 mm to 20 mm, and in one particular embodiment is 5 mm.

Figure 3:
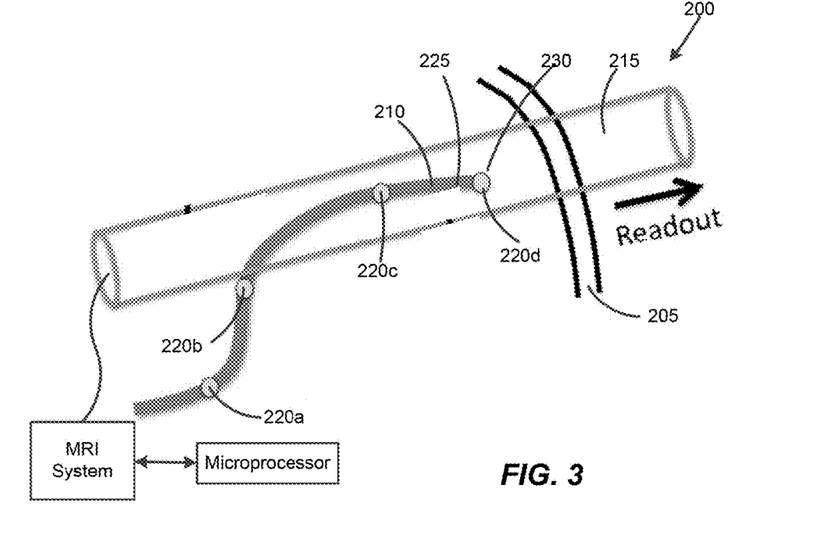
FIG. 3 shows a diagram of one possible geometry of the disclosed system.

FIG. 3 shows a diagram of a system 200 for performing real-time MRI-guided RF ablation according to embodiments of the invention. Shown are the atrial wall 205, the catheter 210, and the pencil beam 215. The position of the catheter 210 may be monitored using a variety of techniques; in the embodiment shown in FIG. 3, the position and approximate shape of the catheter 210 is tracked using information provided by several tracking coils (four in the illustrated embodiment) 220a-220d attached to various portions of the catheter 210.

The positioning of the pencil-beam 215, such that it extends through the catheter tip 225 and approximately perpendicular to the atrial wall 205 as shown in FIG. 3, is possible due to the real-time tracking of the catheter 210 and the acquisition of a 3D MR angiography scan at the start of the procedure. The pencil beam 215 is adjusted so that it is concentric with the distal end 225 of the catheter 210 and approximately perpendicular to the structure in question, e.g. the atrial wall 205. The pencil beam 215 can then provide accurate (e.g. 1-2 mm resolution) information about the position of the wall 205 or other structure at a relatively high frequency (e.g. in a range of 5-100 Hz) which can be combined with information about the position of the catheter tip 225 to help a user guide the catheter 210 and to know if and when the catheter 210 is about to touch the wall 205 or other structure.

Figure 4:
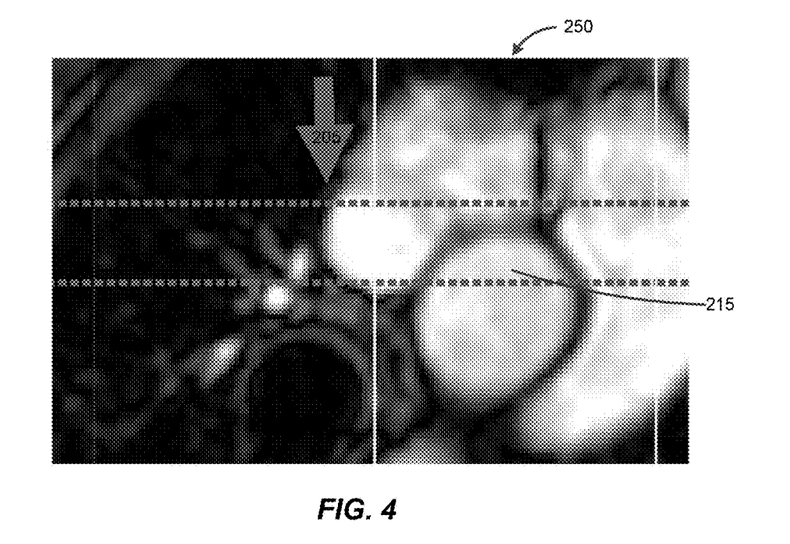
FIG. 4 shows the position of navigator (dotted lines) and right atrial RA wall (arrow)
Figure 5:
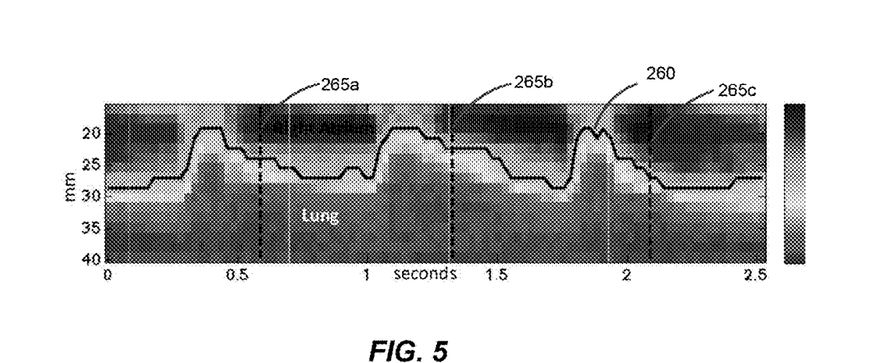
FIG. 5 shows an M-mode display of cardiac wall position obtained using a pencil beam navigator over several cardiac cycles, the position being identified using automatic wall detection of RA wall (indicated by the black wavy line).
Figure 6A:
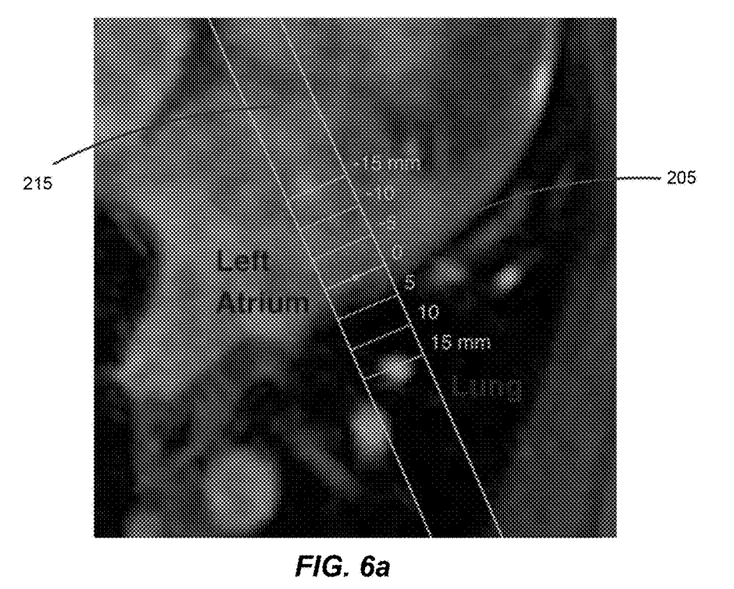
FIG. 6a shows a conventional cine image frame showing the MRI pencil beam position of the same slice as shown in FIG. 6b.
Figure 6B:
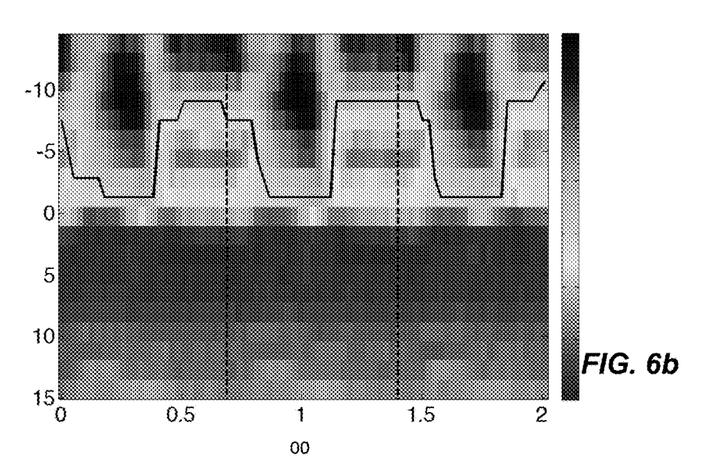
FIG. 6b shows an "M-mode" display obtained from an MRI pencil beam navigator, indicating the position of the atrial wall ("wall") as a function of time, where the left atrium ("LA") is at the top of the graph and the lung is at the bottom of the graph.
Figure 7A:
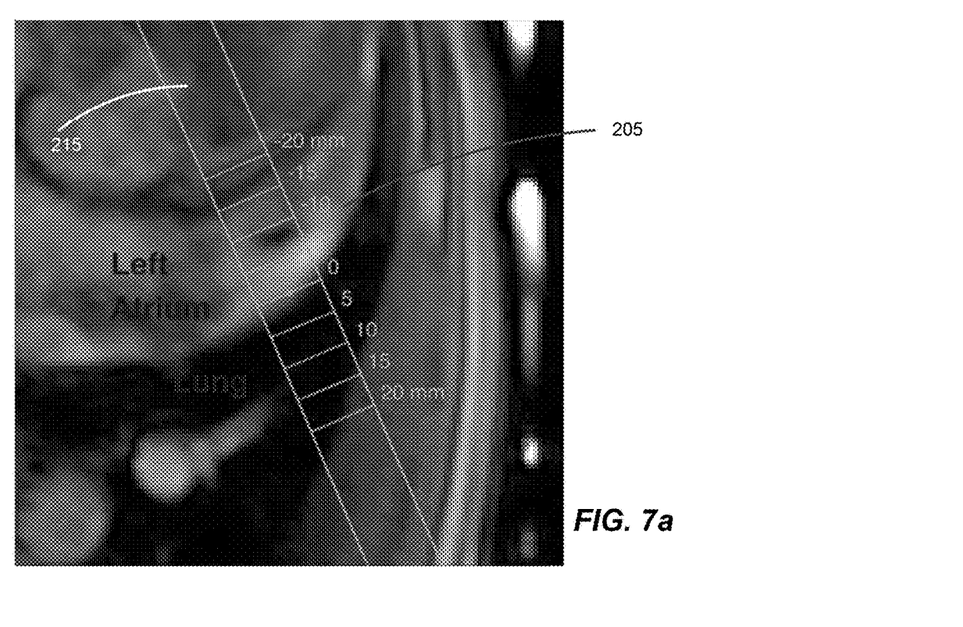
FIG. 7a shows a conventional cine image frame showing the MRI pencil beam position of the same slice as shown in FIG. 7b.
Figure 7B:
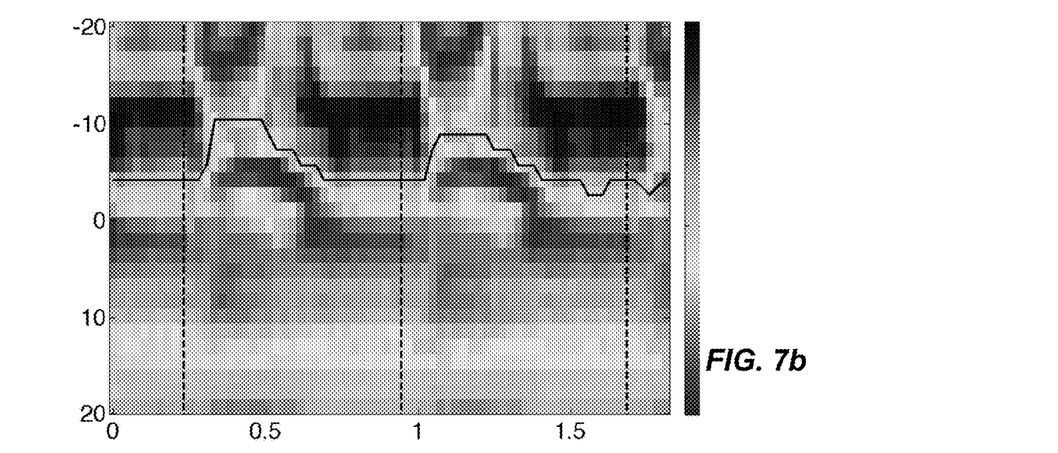
FIG. 7b shows an "M-mode" display obtained from an MRI pencil beam navigator, indicating the position of the atrial wall ("wall") as a function of time, where the left atrium ("LA") is at the top of the graph and the lung is at the bottom of the graph.

FIGS. 4 and 5 demonstrate the use of the pencil-beam navigator 215 (generated using TE/TR=3.5/25 ms, 8° flip angle, providing 1.5 mm readout resolution) to detect the location of the right atrial wall 205 in a pig in a 3 Tesla scanner. FIG. 4 shows the position of the pencil-beam 215 overlaid on a slice 250 of the MR angiography image, where the 5-mm radius pencil-beam 215 is indicated by the dotted lines and intersects the wall 205 of the right atrium, which is indicated by the arrow. FIG. 5 shows the signal from the navigator 215 in an M-mode display which plots distance along the pencil-beam versus time. The navigator is acquired continuously over more than three heartbeats at about 40 frames per second (40 Hz). The automatic detection of the wall, denoted by the horizontal wavy line 260, is performed by finding the center of the edge in the known neighborhood of the atrial wall 205. The vertical dashed lines 265a-265c denote the R-wave detected from the concurrently acquired ECG signal and are seen to match the periodicity of motion of the wall 205. FIGS. 6a, 6b, 7a, and 7b show results of in vivo canine experiments in which the position of the left atrial wall-lung interface is monitored using a 5 mm cylindrical pencil beam navigator 215. Continuous acquisition was performed over a period of several heartbeats. The scale of the M-mode display data is superimposed on the cine image to provide an indication of how far the cardiac wall traverses in each cardiac cycle.

The disclosed MRI-based methods and systems provide several benefits over current X-ray and ultrasonic technologies for obtaining position information during RF ablation and similar procedures. Compared to X-ray methods, using MRI eliminates exposure to ionizing radiation. In addition, the disclosed methods and systems provide better catheter navigation as a result of real-time catheter tracking, better soft-tissue imaging, and the ability to generate arbitrary views. The disclosed methods and systems also provide improved ablation verification and provide information about the state of the ablated tissue using T1 and T2 relaxation times, and MRI thermometry. Finally, improved accuracy associated with use of the disclosed methods and systems provides reduced collateral structural damage.

Accordingly, disclosed are methods and systems for detecting atrial wall motion in vivo, using a pencil-beam navigator in order to monitor tip-tissue contact during real-time-MRI-guided RF ablation. In various embodiments, the disclosed methods and systems may be incorporated into a real-time, interactive sequence and combined with existing catheter tracking methods in order to monitor tip-tissue contact in real-time. Further optimizations, such as of the length and profile of the RF pulse, the automatic positioning of the pencil-beam, the relative timing of the acquisition of catheter tracking data, and the most effective visualization of the information, may also be integrated with the disclosed methods and systems. In still further embodiments, a 2D echoplanar projection readout of the excited pencil-beam volume may be used instead of, or in addition to, 1D projections as disclosed herein. Other embodiments may employ bSSFP-like, instead of GRE-like, blood-tissue contrast by adjusting the gradient moments accordingly. In various embodiments the disclosed methods and systems may include fully automated detection of the target structure (e.g. atrial wall). Further, various embodiments may incorporate a priori information, such as a pre-acquired atrial shell, into the placement of the navigator beam and the detection of the wall or other structure.

In various embodiments, the invention includes systems for carrying out the procedures disclosed herein. The system may include an MRI system, a catheter, and a controller. The controller may be contained in one or several units and may include a computing system having a microprocessor for executing software instructions as well as input and output capabilities including a keyboard, mouse, and display, and may be coupled to one or more other computers via a network such as a local network and/or a global network such as the Internet.

Thus, the invention provides, among other things, methods and systems for real-time-MRI-guided radiofrequency (RF) cardiac tissue ablation. Various features and advantages of the invention are set forth in the following claims.

What is claimed is:

1. A method of monitoring a position of a catheter tip relative to a target tissue, the method comprising the steps of:
   identifying, using a magnetic resonance imaging (MRI) system, a wall structure in the target tissue;
   monitoring in real time, with a position tracking system of a catheter, a location of the catheter;
   generating, with the magnetic resonance imaging system, a pencil beam directed towards the wall structure;
   adjusting, automatically with the magnetic resonance imaging system, the pencil beam such that the pencil beam is concentric with a tip at a distal end of the catheter and is approximately perpendicular to the wall structure;
   monitoring, with a microprocessor, a position of the wall structure using an acquired signal from a volume of tissue excited by the pencil beam;
   determining, with the microprocessor, the position of the wall structure relative to the location of the catheter based on the real time location of the catheter and the position of the wall structure;
   detecting, with the microprocessor, a tip-tissue contact based on the position of the wall structure relative to the location of the tip at the distal end of the catheter;
   displaying data acquired from the pencil beam in an M-mode display and the real time location of the catheter.

2. The method of claim 1, wherein monitoring a location of the catheter comprises monitoring a location of the catheter using a plurality of coils of the position tracking system attached to the catheter.

3. The method of claim 1, wherein the data acquired from the pencil beam includes the position of the wall structure relative to the location of the catheter.

4. The method of claim 1, wherein directing a pencil beam towards the wall structure comprises adjusting the pencil beam to be approximately perpendicular to the wall structure.

5. The method of claim 1, further comprising measuring electrical activity in the target tissue using the catheter.

6. The method of claim 1, wherein monitoring a position of the wall structure using the pencil beam comprises monitoring a position of the wall structure using the pencil beam at a rate of at least 40 Hz.

7. The method of claim 1, wherein the target tissue comprises cardiac tissue and wherein the wall structure comprises an atrial wall.

8. The method of claim 1, wherein determining the position of the wall structure relative to the location of the catheter includes determining a center of an edge in a neighborhood associated with a cardiac wall.

9. The method of claim 8, wherein displaying data acquired from the pencil beam includes displaying a line indicative of the wall structure, the line displayed over the center of the edge in the neighborhood associated with the cardiac wall.

10. The method of claim 1, wherein the step of adjusting further comprises adjusting the pencil beam such that the pencil beam is concentric with an axis of the tip at a distal end of the catheter.

11. A system for monitoring a position of a catheter tip relative to a target tissue, the system comprising:
   a magnetic resonance imaging (MRI) system;
   a catheter including a position tracking system and an ablation electrode at a distal end tip of the catheter;
   a display; and
   a microprocessor in communication with the MRI system, the display, and the catheter, the microprocessor configured to:
      identify, with the magnetic resonance imaging system, a wall structure in the target tissue,
      monitor in real time, with the position tracking system, a location of the catheter during guidance of the catheter towards the wall structure and during ablation procedures,
      control the magnetic resonance imaging system to generate a pencil beam directed towards the wall structure,
      control the magnetic resonance imaging system to automatically adjust the pencil beam direction such that the pencil beam is concentric with the distal end tip of the catheter and is approximately perpendicular to the wall structure in the target tissue,
      report a position of the wall structure using an acquired signal from a volume of tissue excited by the pencil beam,
      determine the position of the wall structure relative to the location of the catheter based on the real time location of the catheter and the position of the wall structure,
      detect a tip-tissue contact based on the position of the wall structure relative to the location of the catheter,
      control the display to display data acquired from the pencil beam in an M-mode display and the location of the catheter.

12. The system of claim 11, wherein the position tracking system of the catheter comprises a plurality of coils attached to the catheter.

13. The system of claim 11, wherein the data acquired from the pencil beam includes the position of the wall structure relative to the location of the catheter.

14. The system of claim 11, wherein the microprocessor, in order to direct the pencil beam towards the wall structure, is further configured to adjust the pencil beam to be approximately perpendicular to the wall structure.

15. The system of claim 11, the microprocessor further configured to measure electrical activity in the target tissue using the catheter.

16. The system of claim 11, wherein the microprocessor is configured to report a position of the wall structure using the pencil beam at a rate of at least 40 Hz.

17. The system of claim 11, wherein the microprocessor determines the position of the wall structure by determining a center of an edge near a region associated with a cardiac wall.

18. The system of claim 17, wherein the microprocessor displays a line indicative of the cardiac wall over the data acquired from the pencil beam.

19. The system of claim 11, wherein the microprocessor is further configured to control the magnetic resonance imaging system to automatically adjust the pencil beam such that the pencil beam is concentric with an axis of a tip of the catheter and at the location of the catheter.

* * * * *